(12) United States Patent
Kim et al.

(10) Patent No.: US 11,666,392 B2
(45) Date of Patent: Jun. 6, 2023

(54) DEVICE FOR GUIDING POSITION OF ROBOT, METHOD THEREFOR, AND SYSTEM INCLUDING THE SAME

(71) Applicant: CUREXO, INC., Seoul (KR)

(72) Inventors: Bong Oh Kim, Seoul (KR); Soo Jong Kim, Seoul (KR); Geun Young Kim, Seoul (KR); Yong Hee Han, Seoul (KR); Heung Soon Lim, Seoul (KR)

(73) Assignee: CUREXO, INC., Seoul (KR)

( * ) Notice: Subject to any disclaimer, the term of this patent is extended or adjusted under 35 U.S.C. 154(b) by 0 days.

(21) Appl. No.: 17/640,509

(22) PCT Filed: Sep. 3, 2020

(86) PCT No.: PCT/KR2020/011895
§ 371 (c)(1),
(2) Date: Mar. 4, 2022

(87) PCT Pub. No.: WO2021/045546
PCT Pub. Date: Mar. 11, 2021

(65) Prior Publication Data
US 2022/0265364 A1    Aug. 25, 2022

(30) Foreign Application Priority Data

Sep. 5, 2019    (KR) .................. 10-2019-0109922

(51) Int. Cl.
*A61B 34/20*    (2016.01)
*A61B 34/00*    (2016.01)
(Continued)

(52) U.S. Cl.
CPC .............. *A61B 34/20* (2016.02); *A61B 34/25* (2016.02); *A61B 34/30* (2016.02); *A61B 90/37* (2016.02);
(Continued)

(58) Field of Classification Search
CPC ................. A61B 34/25; A61B 2034/252–258
See application file for complete search history.

(56) References Cited

U.S. PATENT DOCUMENTS 10,368,878 B2 *    8/2019    Lavallee ................. A61B 34/70
10,441,294 B2 *    10/2019    Lavallee ................. B25J 9/0009
(Continued)

FOREIGN PATENT DOCUMENTS

CN    112770687 A  *  5/2021    ............ A61B 34/20
KR    10-2010-0023086 A    3/2010
(Continued)

*Primary Examiner* — Angela M Hoffa
(74) *Attorney, Agent, or Firm* — Bridgeway IP Law Group, PLLC; Jihun Kim

(57) ABSTRACT

Proposed are a device for guiding the position of a robot, a method thereof, and a system including the same, the device including a surgical target matcher configured to derive a correlation of a position and a posture between a surgical target and a target marker attached to the surgical target, a robot matcher configured to derive a correlation of a position and a posture between a robot maker and a surgical robot based on an image including the robot marker mounted to the surgical robot and derive a correlation of a position and a posture between the robot marker and a preset work space, and a work space identifier configured to derive a correlation of a position and a posture between the surgical target and the work space based on information about the positions and postures of the target marker and the robot marker.

11 Claims, 7 Drawing Sheets

(51) Int. Cl.
*A61B 34/30* (2016.01)
*A61B 90/00* (2016.01)

(52) U.S. Cl.
CPC ...... *A61B 90/39* (2016.02); *A61B 2034/2055* (2016.02); *A61B 2034/254* (2016.02); *A61B 2090/3916* (2016.02)

(56) References Cited

U.S. PATENT DOCUMENTS

| | | | |
|---|---|---|---|
| 10,667,868 B2* | 6/2020 | Malackowski | A61B 34/30 |
| 10,864,050 B2* | 12/2020 | Tabandeh | A61B 90/39 |
| 11,051,894 B2* | 7/2021 | Farritor | A61B 90/361 |
| 11,154,369 B2* | 10/2021 | Roldan | A61B 34/10 |
| 11,183,297 B2* | 11/2021 | Moctezuma de la Barrera | A61B 17/154 |
| 2008/0269599 A1 | 10/2008 | Csavoy et al. | |
| 2010/0210939 A1 | 8/2010 | Hartmann et al. | |
| 2016/0113720 A1* | 4/2016 | Lavallee | A61B 17/15 901/9 |
| 2016/0135816 A1* | 5/2016 | Lavallee | B25J 9/0009 606/88 |
| 2016/0157887 A1 | 6/2016 | Kim et al. | |
| 2019/0069962 A1 | 3/2019 | Tabandeh et al. | |
| 2019/0090965 A1* | 3/2019 | Farritor | A61B 34/25 |
| 2019/0223962 A1* | 7/2019 | Roldan | A61B 34/30 |
| 2020/0069373 A1* | 3/2020 | Yu | A61B 34/20 |
| 2020/0093500 A1* | 3/2020 | Lavallee | B25J 9/0009 |
| 2020/0405394 A1* | 12/2020 | Roldan | A61B 34/10 |
| 2021/0205037 A1* | 7/2021 | Tabandeh | A61B 34/32 |
| 2021/0330404 A1* | 10/2021 | Farritor | A61B 90/361 |
| 2022/0031412 A1* | 2/2022 | Roldan | A61B 34/30 |

FOREIGN PATENT DOCUMENTS

| | | |
|---|---|---|
| KR | 10-2016-0069180 A | 6/2016 |
| KR | 10-1817438 B1 | 1/2018 |
| KR | 10-2018-0113512 A | 10/2018 |
| WO | WO-2021257681 A1 * | 12/2021 |

* cited by examiner

DEVICE FOR GUIDING POSITION OF ROBOT, METHOD THEREFOR, AND SYSTEM INCLUDING THE SAME

TECHNICAL FIELD

The disclosure relates to a device for guiding the position of a robot, a method thereof, and a system including the same, and more particularly to a device, method and system for guiding the positions and postures of a surgical target and a robot by deriving a work space from the positions and postures of the surgical target and robot.

BACKGROUND ART

With recent development of medical technology, navigation surgery using a robot and a computer system has actively been introduced, and such surgery has been applied even to the field of artificial joint surgery.

In the case of a knee joint, a whole- or partial-replacement operation based on orthopedic surgery is used in treating the joint when patients feel pains and have behavior disorder due to external injury or various infections and diseases, and about 10 to 30% of the patients undergo a knee-joint partial-replacement operation because their inner knee joints have worn out.

Among robots used in the orthopedic surgery for the joint, there is a robot that automatically performs all surgical procedures, and such a surgical robot automatically cuts a bone without human intervention along a path planned in advance.

When a conventional robot for the orthopedic surgery is used in performing a knee-joint operation, an operation path is determined in advance, an optical marker is mounted to a surgical target, the position and posture of the optical marker are tracked by an optical sensor, and the operation is performed while monitoring a patient's position and the robot's position based on the operation path.

Meanwhile, according to the positions and postures of the surgical robot or the position and posture of the bone, the operation path may be out of an area that an end effector of an arm of the robot can reach, or the robot may make a kinematic error while moving along a moving path.

However, a work space of the robot is identifiable only after setting a start position of the robot, and therefore the robot may not reach a required operation position during the operation, thereby causing a problem that the operation is stopped.

DISCLOSURE

Technical Problem

Accordingly, the disclosure is proposed to solve the foregoing problem, and an aspect of the disclosure is to provide a system and method for identifying whether a robot is in an operable position and posture corresponding to an operation path before an operation.

Further, the disclosure is proposed to solve the foregoing problem, and an aspect of the disclosure is to provide a system and method for guiding the position and posture of a robot to be positioned in a work space.

Further, the disclosure is proposed to solve the foregoing problem, and an aspect of the disclosure is to provide a system and method for guiding the position and posture of a surgical target to be in a work space of a robot.

Technical Solution

According to an aspect of the disclosure, a device for guiding a position of a robot includes: a surgical target matcher configured to derive a correlation of a position and a posture between a surgical target and a target marker attached to the surgical target by matching between an image including the target marker attached to the surgical target and a surgical target image of the surgical target of before an operation; a robot matcher configured to derive a correlation of a position and a posture between a robot maker and a surgical robot based on an image including the robot marker mounted to the surgical robot, and derive a correlation of a position and a posture between the robot marker and a preset work space; and a work space identifier configured to derive a correlation of a position and a posture between the surgical target and the work space based on information about the positions and postures of the target marker and the robot marker.

According to an aspect of the disclosure, a method of guiding a position of a robot includes:

deriving a correlation of a position and a posture between a surgical target and a target marker attached to the surgical target by matching between an image including the target marker attached to the surgical target and a surgical target image of the surgical target of before an operation; deriving a correlation of a position and a posture between a robot maker and a surgical robot based on an image including the robot marker mounted to the surgical robot, and deriving a correlation of a position and a posture between the robot marker and a preset work space; and deriving a correlation of a position and a posture between the surgical target and the work space based on information about positions and postures of the target marker and the robot marker; and displaying an image by generating a graphic based on guide information about the correlation of the position and the posture between the surgical target and the work space.

According to an aspect of the disclosure, a system for guiding a position of a robot includes: a tracker configured to track positions and postures of a robot marker mounted to a surgical robot and a target marker attached to a surgical target; a memory configured to store a surgical target image of the surgical target, obtained before an operation; a surgical target matcher configured to derive a correlation of a position and a posture between the surgical target and the target marker attached to the surgical target based on the surgical target image; a robot matcher configured to derive a correlation of a position and a posture between the robot marker and the surgical robot, and derive a correlation of a position and a posture between the robot marker and a preset work space; a work space identifier configured to a correlation of a position and a posture between the work space and the surgical target based on information about the positions and postures of the target marker and the robot marker obtained by the tracker; a graphic user interface (GUI) generator configured to generate a graphic based on guide information about the correlation of the posture and the posture between the work space and the surgical target; and a display configured to display an image based on the guide information.

Advantageous Effects

As described above, according to the disclosure, it is possible to identify whether the position and posture of a surgical target are within a work space of a surgical robot. Further, according to the disclosure, the robot is guided to move to work position and posture spaces, thereby minimizing a risk that an operation will be stopped. Further, according to the disclosure, the posture of the surgical target is guided to the work posture space of the robot, and thus the operation is smoothly performed.

MODE FOR INVENTION

Below, exemplary embodiments of the disclosure will be described with reference to the accompanying drawings. However, details of the publicly known functions or configurations, which may cloud the gist of the disclosure, will be omitted from the following descriptions and the accompanying drawings. Further, if possible, like numerals refer to like elements throughout the accompanying drawings.

The terms or words, which are used in the specification and claims to be described below, should not be construed as having typical or dictionary meanings, but be construed in conformity with the technical idea of the disclosure on the principle that the inventor(s) can appropriately define terms in order to describe his or her invention in the best way. Therefore, embodiments described in the specification and features illustrated in drawings are merely exemplary embodiments of the disclosure and do not represent all the technical idea of the disclosure, and thus it should be understood that there may be various substitutive equivalents and modifications at the filing date of the present application.

Below, a system and device for guiding the position of a robot according to an embodiment of the disclosure will be described with reference to FIGS. 1 to 5.

Figure 1:
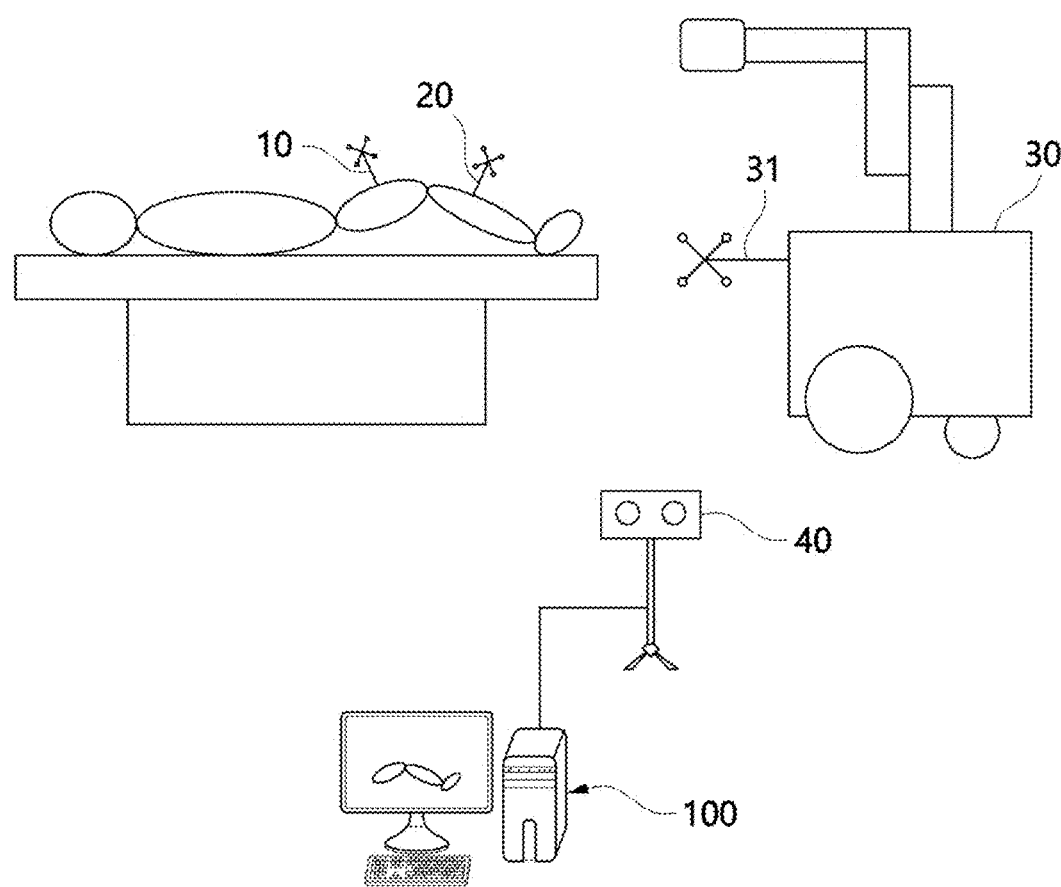
FIG. 1 schematically illustrates a system for guiding the position of a robot according to an embodiment of the disclosure.

FIG. 1 schematically illustrates a position guide system for a robot according to an embodiment of the disclosure. Referring to FIG. 1, the position guide system for the robot according to an embodiment of the disclosure includes target markers (or bone markers) 10 and 20 attached to surgical targets 1 and 2, a surgical robot 30, a tracker 40, and a position guide device 100.

The surgical targets 1 and 2 refer to targets to have an operation. According to an embodiment of the disclosure, it will be described by way of example that the surgical targets are a femur 1 and a tibia 2 between which a knee joint is positioned, and thus the target markers 10 and 20 are respectively attached to the femur 1 and the tibia 2.

The surgical robot 30 is to perform a joint operation. The surgical robot 30 may include a robot base and a robot arm, and a cutting tool may be positioned at an end effect of the arm. A robot marker 31 is mounted to the base of the surgical robot 30.

Optical markers may be employed as the target markers 10 and 20 and the robot marker 31, and include three or four bars branched from a central point in different directions. At the end of the bar, a highly-reflective ball marker may be formed.

The tracker 40 is to track the positions and postures of the robot marker 31 mounted to the surgical robot 30 and the target markers 10 and 20 attached to the surgical targets. The tracker 40 detects the positions and postures of the markers on three-dimensional (3D) coordinates, and transmits the detected positions and postures to the position guide device 100 (to be described later). According to an embodiment of the disclosure, it will be described by way of example that the tracker 40 is embodied as an optical tracking system (OTS).

The position guide device 100 is to perform matching for the surgical targets and matching for the surgical robot 30 based on signals received from the tracker 40, and guide the position of the surgical robot 30 based on a correlation of the position/posture between the work space of the surgical robot 30 and the surgical targets 1 and 2. As shown in FIG. 1, the position guide device 100 may include a computer or microprocessor, and a display. FIG. 1 shows that the position guide device 100 is embodied as an additional device separated from the surgical robot 30. As necessary, the computer or microprocessor of the position guide device may be provided in the surgical robot 30, and the display of the position guide device may be installed as connected to the tracker 40. In this case, the surgical robot 30 is connected to the tracker 40, receives position/posture information about the markers from the tracker 40, and processes and transmits the position/posture information to the display.

Figure 2:
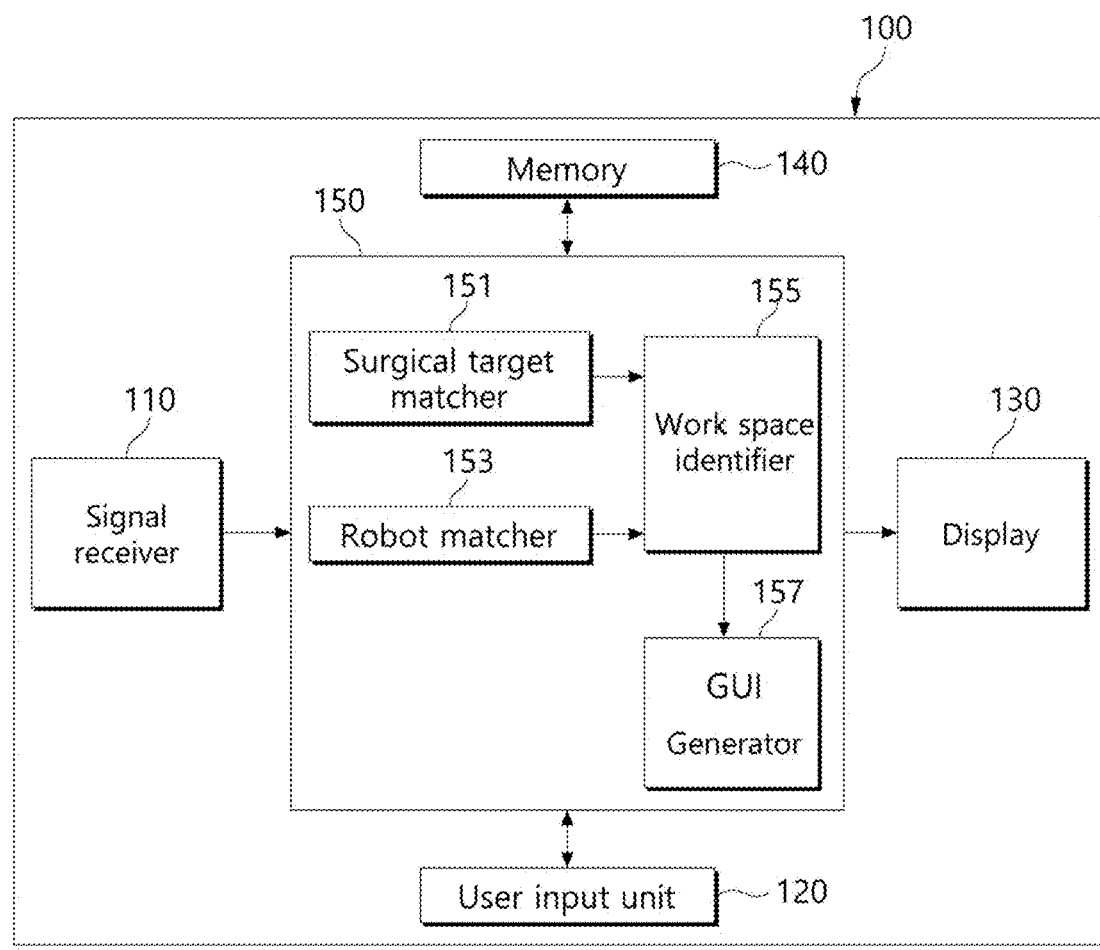
FIG. 2 is a control block diagram of a position guide device according to an embodiment of the disclosure.

FIG. 2 is a control block diagram of the position guide device 100 according to an embodiment of the disclosure. Referring to FIG. 2, the position guide device 100 according to an embodiment of the disclosure includes a signal receiver 110, a user input unit 120, a display 130, a memory 140, and a controller 150.

The signal receiver 110 is to receive a signal from the outside. For example, the signal receiver 110 may include a high-definition multimedia interface (HDMI) connector 11 or a D-sub connector for connection with an external device, or a communication module for connection with a wired/wireless network such as the Internet. The signal receiver 110 may include a wired/wireless communication module for interworking between the tracker 40 and the surgical robot 30.

The user input unit 120 is to receive a command from a user and input the command to the controller 150 (to be described later). The user input unit 120 may include at least one of various user input units such as a keyboard, a mouse, a button, etc.

The display 130 is to display an image on a screen. The display 130 may be embodied with a liquid crystal display (LCD) panel, a light emitting diode (LED) panel, an organic light emitting diode (OLED) panel, etc.

The memory 140 is configured to store various operating systems (OS), middleware, a platform, and various applications for the position guide device 100, and store a program code, processed video and audio signals, and data. The memory 140 is configured to store a surgical target image obtained before an operation, for example, a patient's computerized tomography (CT) image, etc. The memory 140 may be embodied by a read only memory (ROM), an erasable programmable read-only memory (EPROM), a random-access memory (RAM), etc.

The controller 150 is in charge of general control of the position guide device 100 based on a user command input through the user input unit 120 or an internal program. The controller 150 may include a program code for signal processing and controlling, and a microprocessor for executing a computer program. The controller 150 performs image matching and position tracking based on the position/posture information received from the tracker 40 through the signal receiver 110, derives a correlation of the work space between the surgical target and the surgical robot 30, and gives guide information for guiding the position and posture of the surgical robot 30 to a user.

Referring to FIG. 2, the controller 150 includes a surgical target matcher 151, a robot matcher 153, a work space identifier 155, and a graphic user interface (GUI) generator 157.

The surgical target matcher 151 is configured to derive a correlation of the position/posture between the surgical targets 1 and 2 and the target markers (or bone markers) 10 and 20 attached to the surgical targets 1 and 2 through image matching. After attaching the target markers 10 and 20 to the surgical target, a probe is used to recognize the positions and postures of the surgical targets and the target markers 10 and 20. The surgical target matcher 151 is configured to receive an optical image about the position and posture indicated by the probe through the tracker 40, and match the received optical image with a patient's 3D data, e.g., CT image previously stored in the memory 140, thereby deriving a correlation of the position/posture between the target markers 10 and 20 and the surgical targets. The surgical target matcher 151 may be embodied by a software algorithm for image matching.

Figure 3:
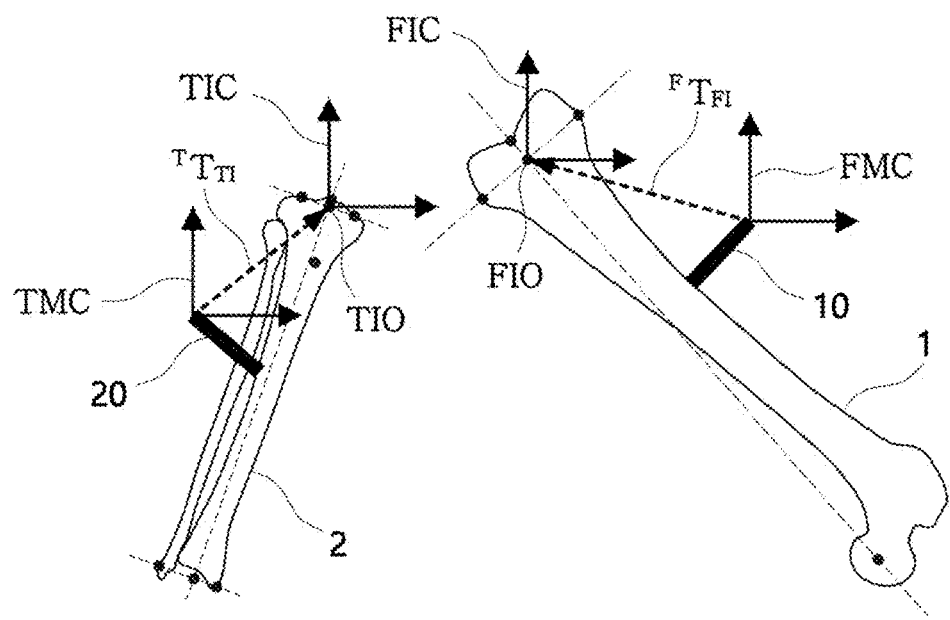
FIG. 3 is a diagram for describing operations of a surgical target matcher according to an embodiment of the disclosure.

FIG. 3 is a diagram for describing operations of the surgical target matcher 151 according to an embodiment of the disclosure. Referring to FIG. 3, the surgical targets are a femur 1 and a tibia 2 between which a knee joint is positioned, and the target markers 10 and 20 are respectively attached to the femur 1 and the tibia 2.

In FIG. 3, femur implant coordinates (FIC) refer to a coordinate system based on the position and posture of a femur implant origin (FIO), and femur marker coordinates (MFC) refer to a coordinate system based on the position and posture of the femur marker 10. Here, the femur implant origin refers to the origin of an operation path, i.e., a cutting path for the femur.

The surgical target matcher 151 may be configured to obtain information about the positions and postures of the femur 1 and the femur marker 10 while scraping the femur 1 with the probes being in contact with the femur 1 at a plurality of points, and match the obtained information with the CT image, thereby deriving a correlation of the position/posture between the femur marker 10 and the FIO, for example, a transformation matrix $^{F}T_{FI}$ as a coordinate transformation relation of the position/posture between the coordinate system of the femur marker 10 and the coordinate system (FIC) based on the FIO. Thus, when the information about the position and posture of the femur marker 10 is obtained from the tracker 40, the controller 150 can derive the position and posture of the femur 1, such as the implant origin of the femur 1, by multiplying the information about the position and posture of the femur marker 10 and the transformation matrix $^{F}T_{FI}$ derived by the surgical target matcher 151.

In FIG. 3, tibia implant coordinates (TIC) refer to a coordinate system based on the position and posture of a tibia implant origin (TIO), and tibia marker coordinates (TFC) refer to a coordinate system based on the position and posture of the tibia marker 20. Here, the implant origin of the tibia 2 refers to the origin of an operation path, i.e., a cutting path.

The surgical target matcher 151 may be configured to obtain information about the positions and postures of the tibia 2 and the tibia marker 20 while scraping the tibia 2 with the probes being in contact with the tibia 2 at a plurality of points, and match the obtained information with the CT image, thereby deriving a correlation of the position/posture between the tibia marker 20 and the TIO, for example, a transformation matrix $^{F}T_{TI}$ as a coordinate transformation relation of the position/posture between the coordinate system of the tibia marker 20 and the coordinate system based on the TIO. Thus, when the information about the position and posture of the tibia marker 20 is obtained from the tracker 40, the controller 150 can derive the position and posture of the tibia 2, such as the implant origin of the tibia 2, by multiplying the information about the position and posture of the tibia marker 20 and the transformation matrix $^{F}T_{TI}$ derived by the surgical target matcher 151.

Here, the positions and postures of the surgical targets, i.e., the femur 1 and the tibia 2 may include the positions and postures of the femur 1 and the tibia 2 at a plurality of points on the operation path, as the meaning including the operation path (e.g., the cutting path) based on the implant origin. In this specification, the 'surgical target' may mean operation targets such as the femur 1 and the tibia 2, etc. in a broad sense, or may mean an implant operation site including the operation path based on the implant origin or the position and posture of the implant origin of the operation target in a narrow sense.

The robot matcher 153 is configured to derive a correlation of the position and posture between the surgical robot 30 and the robot marker 31 mounted to the surgical robot 30, and derive a correlation of the position and posture between the robot marker 31 and a preset work space.

Figure 4:
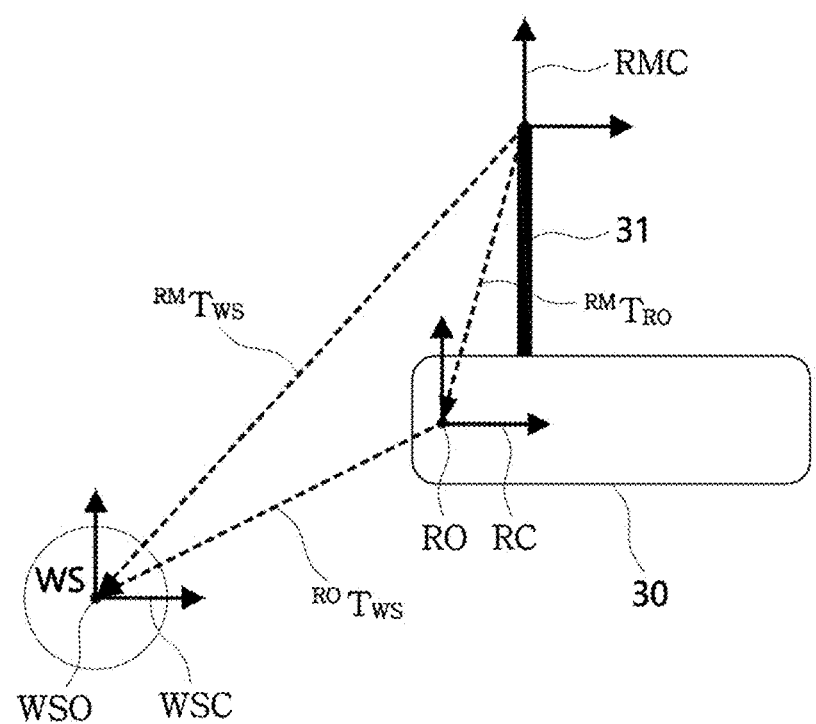
FIG. 4 is a diagram for describing operations of a robot matcher according to an embodiment of the disclosure.

FIG. 4 is a diagram for describing operations of the robot matcher 153 according to an embodiment of the disclosure. Referring to FIG. 4, robot coordinates (RC) refer to a robot coordinate system based on a robot coordinate origin (RO), work space coordinates (WSC) refer to a coordinate system based on the origin of a work space (WS) of the surgical robot 30, and robot marker coordinates (RMC) refer to a coordinate system of the robot marker 31. The WS of the surgical robot 30 refers to a space based on the position and posture of the surgical robot 30, and the correlation of the position/posture between the surgical robot 30 and the work space is previously defined from the origin of the robot coordinate system, and for example has a value of a transformation matrix $^{RO}T_{WS}$ as a coordinate transformation relation of the work space with respect to the origin of the robot coordinate system.

Here, the work space refers to a predefined space calculated based on the information about the position and posture of the surgical robot 30, and includes a work posture space and a work position space. The work position space refers to a space defined to have a certain distance or volume with respect to the origin of the work space, and the work position space is identified based on the posture of the robot. For example, the origin of the work space is calculated as a position previously defined from the position of the robot, and the work position space is set as a space having a certain volume from the origin of the work space. Further, the posture at the origin of the work space may be set the same as the posture of the robot base, and the work posture space may be set as a certain posture range in consideration of a work posture range from the posture at the origin (i.e., the posture of the robot base). For example, the work space refers to a space where the position and posture of a surgical tool mounted to the robot arm are allowable, which may be defined based on the robot base.

The robot matcher 153 is configured to derive a position relation of the origin between the robot marker 31 and the surgical robot 30, i.e., the transformation matrix $^{RM}T_{RO}$ as a coordinate transformation relation of the position/posture between the coordinate system of the robot marker 31 and the coordinate system of the surgical robot 30, based on matching. The robot matcher 153 may be configured to register the position of the surgical robot 30 and the position of the robot marker 31 through the tracker 40, and derive a correlation between the registered positions. By mounting the marker to the robot arm, and tracking the position and posture of the marker through the tracker 40 while the robot arm is moving, the robot matcher 153 can derive the transformation matrix $^{RM}T_{RO}$, i.e., the correlation between the position/posture of the robot base and the position/posture of the robot marker 31.

The robot matcher 153 is configured to derive the correlation of the position/posture between the robot marker 31 and the work space based on the transformation matrix $^{RM}T_{RO}$ of the robot coordinate origin relative to the robot marker 31 and the transformation matrix $^{RO}T_{WS}$ of the work space with respect to the origin of the surgical robot 30. This can be expressed as follows.

$$^{RM}T_{WS} = {}^{RM}T_{RO} \times {}^{RO}T_{WS} \qquad \text{Equation 1}$$

(where, $^{RM}T_{WS}$ is the transformation matrix of the work space for the robot marker 31, $^{RM}T_{RO}$ is the transformation matrix of the origin of the surgical robot 30 with respect to the robot marker 31, and $^{RO}T_{WS}$ is the transformation matrix of the work space with respect to the origin of the surgical robot 30.)

Thus, the controller 150 can obtain the information about the position and posture of the robot marker 31 from the tracker 40, and derive the position and posture of the origin in the robot work space by multiplying the information about the position and posture of the robot marker 31 and the transformation matrix $^{RM}T_{WS}$ derived by the robot matcher 153. The controller 150 is configured to derive the work position space and the work posture space from the position and posture of the origin in the work space. As described above, the work space refers to the work position space defined to have a certain volume from the origin of the work space and the work posture space corresponding to the posture of the surgical robot 30, which may be set based on the position or posture of the surgical robot 30.

The work space identifier 155 may be configured to derive the correlation of the position/posture between the surgical target and the work space based on the information about the positions and postures of the target markers 10 and 20 and the robot marker 31. The work space identifier 155 may be embodied by a software algorithm for the position/posture transformation and calculation.

Figure 5:
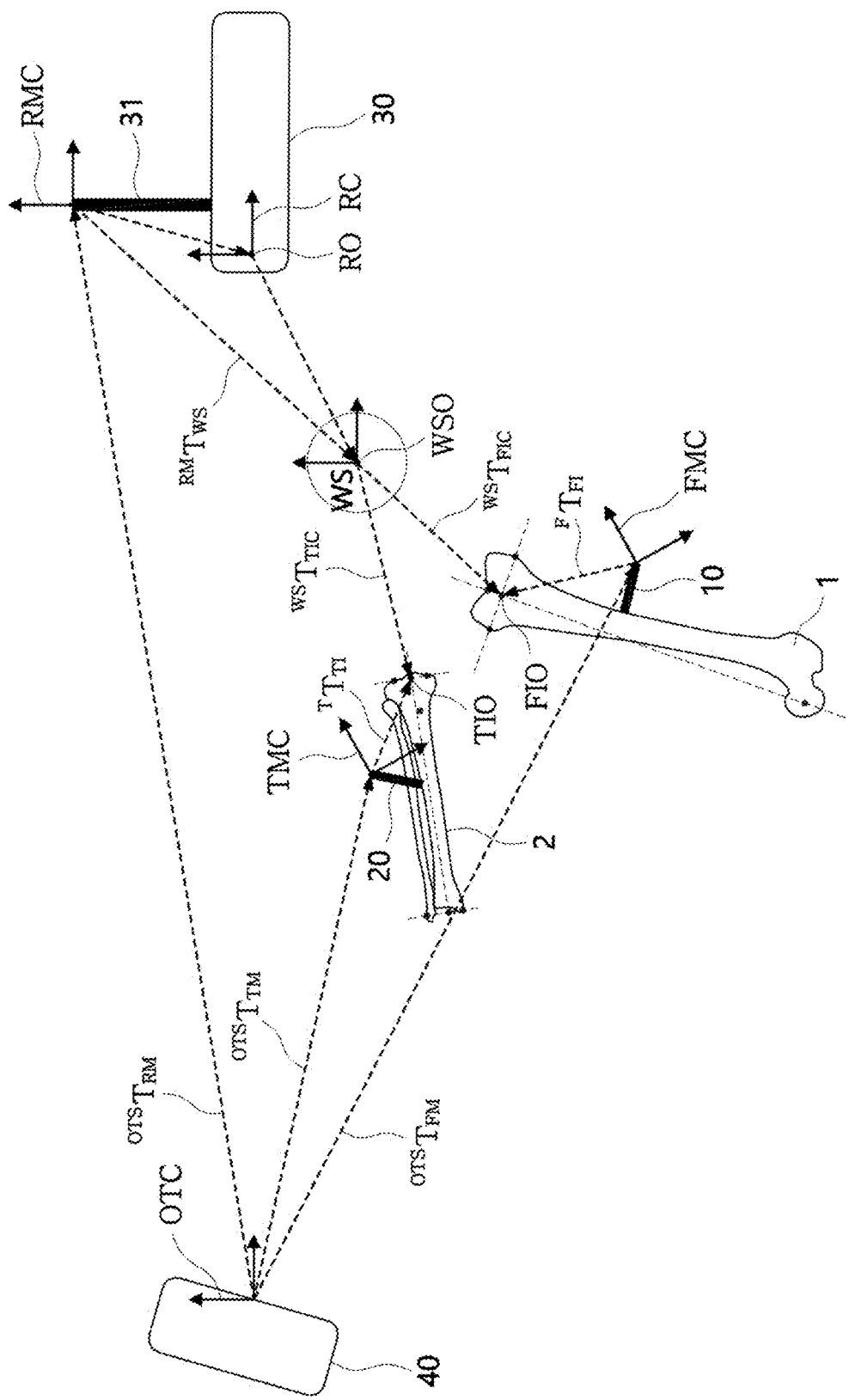
FIG. 5 is a diagram for describing operations of a work space identifier according to an embodiment of the disclosure.

FIG. 5 is a diagram for describing operations of the work space identifier 155 according to an embodiment of the disclosure.

The work space identifier 155 is configured to obtain the information about the position and posture of the robot marker 31 installed in the base of the surgical robot 30 and the position and posture of the target markers 10 and 20 attached to the femur 1 and the tibia 2 through the tracker 40, and identify the correlation of the position/posture between the surgical targets 1 and 2 and the work space of the surgical root 30.

The work space identifier 155 is configured to obtain the information about the positions and postures of the robot marker 31 and the target markers 10 and 20 from the tracker 40. In FIG. 5, OTC indicates the coordinate system of the tracker 40, robot marker coordinates (RMC) indicate the coordinate system of the robot marker 31, femur marker coordinate (FMC) indicate the coordinate system of the femur marker 10, and tibia marker coordinates (TMC) indicate the coordinate system of the tibia marker 20. Both the position/posture information of the femur marker 10 and position/posture information of the tibia marker 20 are obtained from the tracker 40 based on the coordinate system of the tracker 40, so that the positions of the robot marker 31 and the target markers 10 and 20 can be transformed into that in the coordinate system of the tracker 40 based on transformation relationships $^{OTS}T_{RM}$, $^{OTS}T_{TM}$ and $^{OTS}T_{FM}$ among the coordinate system of the tracker 40, the coordinate system of the robot marker 31 and the coordinate system of the target markers 10 and 20.

The work space identifier 155 is configured to multiply multiplying the position and posture information of the femur marker 10 transformed based on the coordinate system of the tracker 40 by the transform matrix $^{F}T_{FP}$, i.e., the correlation of the femur implant origin (FIO) with regard to to the femur marker 10 calculated in the surgical target matcher 151, thereby deriving the position and the posture of the femur 1 in the coordinate system of the tracker 40.

In the same manner, the work space identifier 155 is configured to multiply the position and posture information of the tibia marker 20 transformed based on the coordinate system of the tracker 40 by the transform matrix $^{T}T_{TP}$, i.e., the position/posture correlation of the tibia implant origin with regard to the tibia marker 20 calculated in the surgical target matcher 151, thereby deriving the position and posture of the tibia 2 in the coordinate system of the tracker 40.

The work space identifier 155 is configured to multiply the position and posture information of the robot marker 31 transformed based on the coordinate system of the tracker 40 by the transform matrix $^{RM}T_{WS}$, i.e., the correlation of the work space with regard to the robot marker 31 calculated in the robot matcher 151, thereby deriving the position (i.e., the work position space) and the posture (i.e., the work posture space) of the work space origin in the coordinate system of the tracker 40.

The positions/postures of the femur and the tibia and the position/posture of the work space are all values based on the coordinate system of the tracker 40, so that the work space identifier 155 can drive the correlation of the positions/postures among the femur, the tibia and the work space based on these values. Referring to FIG. 5, the work space identifier 155 derives the correlation of the position and posture between the femur and the work space, e.g., the position transform matrix $^{WS}T_{FIC}$ and the correlation of the position and posture between the tibia and the work space, e.g., the position transform matrix $^{WS}T_{TIC}$.

In FIGS. 3 to 5, the implant origin of the femur 1 and the implant origin of the tibia 2 refer to the origins of the operation path, i.e., the cutting path. The operation path is previously planned before an operation, and may be varied depending on cutting ranges, implant kinds, etc. of the femur and the tibia. Information about the operation path, e.g., the cutting path is previously stored, but the position and posture of the implant origin based on the operation path are relatively defined according to the positions/postures of the surgical target and the surgical robot 30.

Through the foregoing operations according to the disclosure, the work space based on the position/posture of the surgical robot 30 and the operation path based on the position/posture of the surgical target, e.g., the position/posture of the origin of the operation path are calculated, and the correlation between them is calculated.

Figure 6:
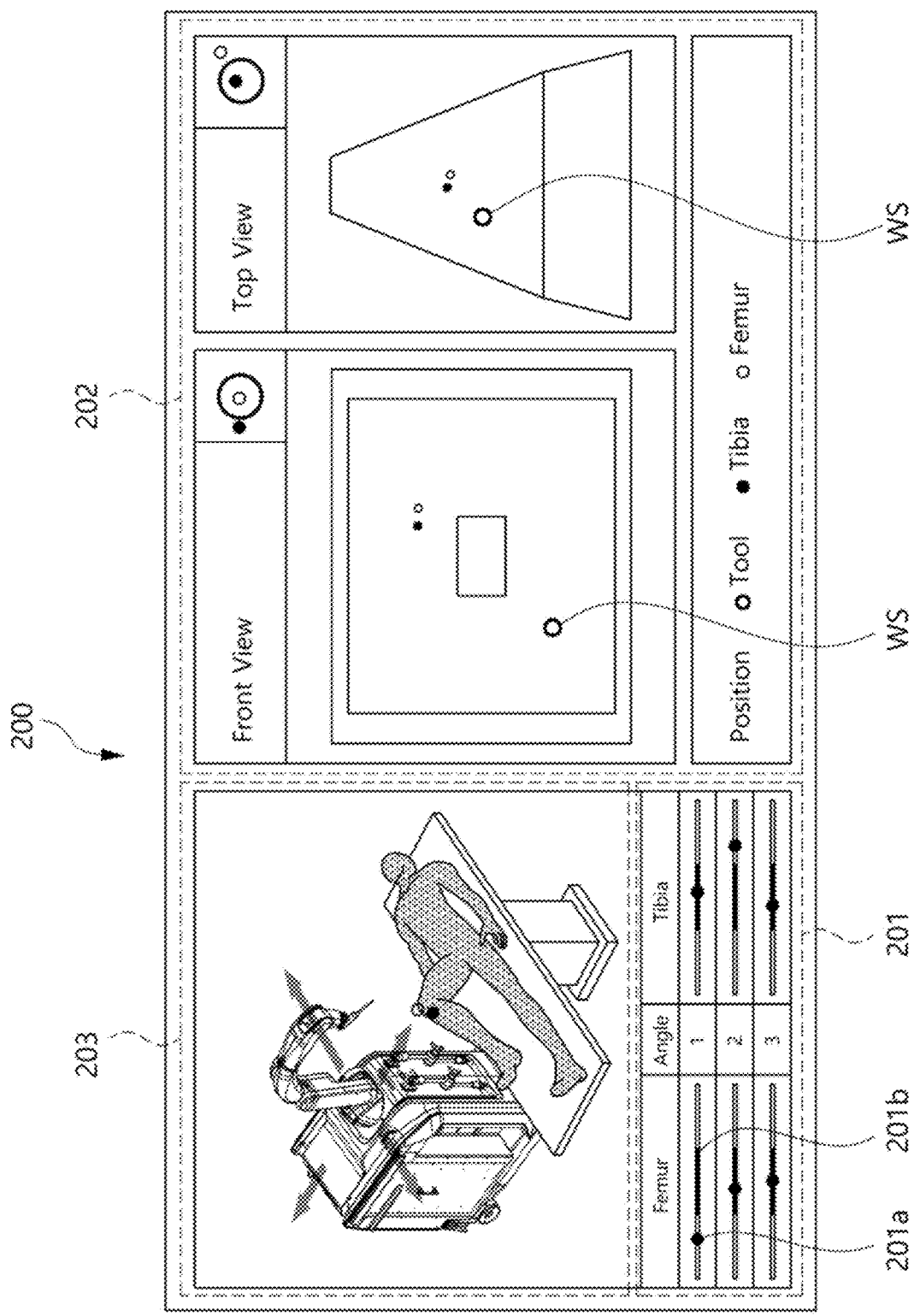
FIG. 6 illustrates an example of guide information generated by a graphic user interface (GUI) generator according to an embodiment of the disclosure.

The GUI generator 157 is configured to generate a graphic based on the guide information about the correlation between the position of the surgical target and the work position space and the correlation between the posture of the surgical target and the work posture space, and transmits the graphic to the display 130. The GUI generator 157 may include a graphic processing module, e.g., a graphic card that processes data to generate an image. FIG. 6 illustrates an example of guide information generated by the GUI generator 157 and displayed on the display 130 according to an embodiment of the disclosure. Referring to FIG. 6, the guide information includes a first menu image 201 for showing whether the postures of the surgical targets 1 and 2 belong to the work posture space, a second menu image 202 for showing whether the positions of the surgical targets 1 and 2 belong to the work position space, and a third menu image 203 for suggesting a moving direction of the surgical robot 30. Further, the guide information may visually show information about a separation distance between the work space and the positions of the surgical targets as shown in the second menu image.

The first menu image 201 graphically shows whether the postures (rotated angles) of the surgical target belong to the work posture space. In the first menu image 201, a point 201a indicates each current posture (rotated angle) of the femur 1 and the tibia 2, and a bar 201b represented with color indicates the work posture space. Therefore, a user may suitably adjust the postures of the surgical targets 1 and 2 or the posture of the surgical robot 30 to belong to the work posture space, while checking whether the points 201a indicating the postures (rotated angles) of the femur 1 and the tibia 2 are within or beyond the color bar 201b indicating the work posture space. As shown in the first menu image 201, the postures of the surgical targets 1 and 2 are represented with three postures of Angle1, Angle2, and Angle3 as the rotated angles with respect to three axes, e.g., an X axis, a Y axis and a Z axis.

The second menu image 202 shows relationships between the position of the work space WS and the positions of the surgical targets 1 and 2. The position relationships include position relationships viewed at various positions such as the front, the top, etc., thereby guiding the surgical robot 30 to move so that the surgical targets 1 and 2 can be positioned in the work space. Referring to FIG. 6, the positions of the surgical targets 1 and 2 may be represented including the implant origins of the surgical targets 1 and 2, and including the areas of the surgical targets 1 and 2 included in the operation path with respect to the origins of the operation path based on a previously planned operation path.

The third menu image 203 schematizes the surgical targets 1 and 2 and the moving directions of the robot, and shows the moving directions of the robot by activating frontward, backward, leftward and rightward arrows based on the relationship between the current positions of the surgical targets 1 and 2 and the surgical robot 30. A user moves the surgical robot 30 in the moving directions visually given as the frontward, backward, leftward and rightward arrows for the surgical robot 30 in the third menu image 203, thereby guiding the surgical targets 1 and 2 to belong to the work space WS.

Here, the correlation between the work space WS and the positions and postures of the surgical targets 1 and 2 may be represented based on the coordinate system of the robot.

Thus, according to the disclosure, correlation information between the work spaces based on the position/posture of the surgical robot 30 (e.g., the work position space and the work posture space) and the position/posture of the operation path based on the position/posture of the surgical targets 1 and 2 is graphically displayed, thereby guiding a user to adjust the positions and postures of the surgical robot 30 and the surgical targets 1 and 2 so that an actual operation area (e.g., the operation path) can be positioned within the work space.

Figure 7:
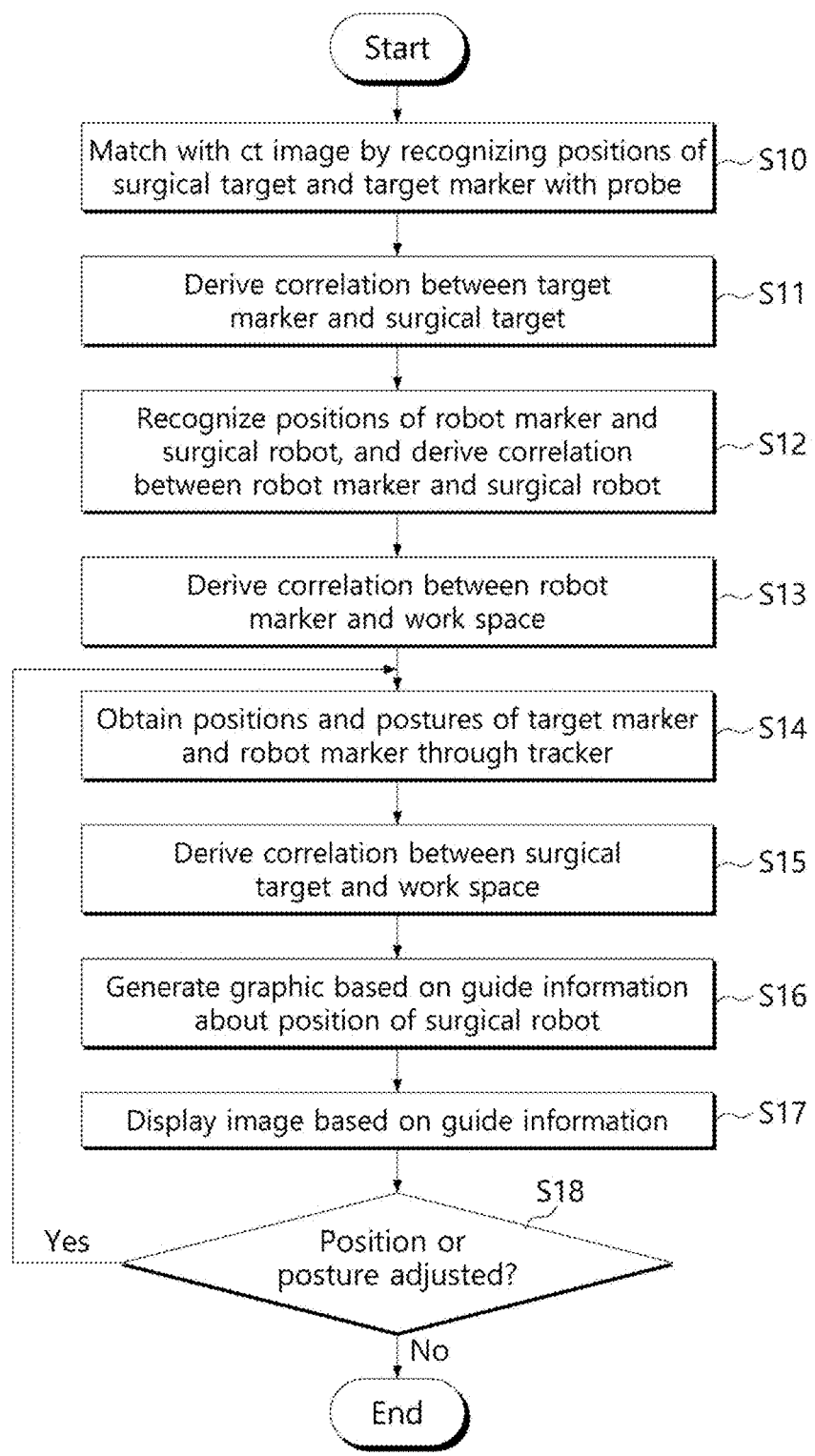
FIG. 7 is a flowchart for describing a position guide method based on a device for guiding the position of a robot according to an embodiment of the disclosure.

FIG. 7 is a flowchart for describing a position guide method based on a position guide device 100 for a robot according to an embodiment of the disclosure. Repetitive descriptions to the foregoing embodiments will be avoided as necessary.

Referring to FIG. 7, the position guide method for the robot according to an embodiment of the disclosure first performs matching with a patient's CT image previously obtained before an operation by a process of recognizing the positions of the surgical targets 1 and 2 and the target markers 10 and 20 with the probe (S10). Through such a matching process, the correlations between the target markers 10 and 20 and the surgical targets 1 and 2 are derived (S11). Further, through the matching process between the robot marker 31 and the surgical robot 30, the correlation of the position/posture between the robot marker 31 and the surgical robot 30 is derived (S12). Further, the correlation between the robot marker 31 and the work space is derived based on the correlation with the work space previously defined by the position/posture of the surgical robot 30 (S13).

The positions and postures of the robot marker 31 and the target markers 10 and 20 are obtained through the tracker 40 (S14), and the correlation of the position and posture between the work space and the position/posture of the surgical targets 1 and 2 is derived based on the correlation of the position and posture between the target markers 10 and 20 and the surgical targets 1 and 2 calculated in the foregoing matching process, and the correlation of the position and posture between the robot marker 31 and the work space (S15).

The GUI generator 157 generates the guide information for guiding the position and posture of the surgical robot 30 (or the surgical target) based on the calculated correlation (S16), and the display 130 displays the guide information as an image (S17).

When the position/posture of the surgical robot 30 or the positions/postures of the surgical targets 1 and 2 is adjusted (S18), the position guide device 100 for the robot receives changed information about the position/posture of the robot marker 31 or the positions/postures of the target markers 10 and 20 through the tracker 40 and performs the foregoing processes S14 to S17, thereby regenerating and displaying guide information based on the adjusted position/posture (S17).

According to an alternative embodiment, the matching processes S12 to S14 for the robot according to the foregoing embodiment shown in FIG. 7 may be performed before the matching processes S10 and S11 for the surgical targets.

With the foregoing processes, the surgical operation starts safely after checking whether the positions/postures of the surgical targets 1 and 2 are within the work space. Thus, according to the disclosure, the surgical robot 30 is guided to move to the work position/posture space, thereby minimizing a risk that an operation will be stopped. In the foregoing embodiments, the correlations of the position/posture between the work space (i.e., the work position space and the work posture space) of the robot and the surgical targets 1 and 2 are derived and visually displayed. However, according to an alternative embodiment, correlations between the position/posture of the robot 30 and the positions/postures of the surgical targets 1 and 2 may be derived and visually displayed.

The work space refers to a space varied depending on the position and posture of the robot, and thus the correlation between the position/posture of the surgical robot 30 and the position/posture of the surgical targets 1 and 2 are derived by the same transformation process as that of the foregoing embodiment. For example, the position and posture of the robot base may be derived instead of the work space, and the current position/posture of the robot and the work position/posture space of the robot base may be displayed based on the positions/postures of the surgical targets 1 and 2, so that a user can guide the robot to move to a target position.

The invention claimed is:

1. A device for guiding a position of a robot, comprising:
at least one processor configured to
derive a first correlation between a position and an orientation of a surgical target and a position and an orientation of a target marker attached to the surgical target by matching an image comprising the target marker attached to the surgical target with a surgical target image of the surgical target of before an operation,
derive a second correlation between a position and an orientation of a robot marker and a position and an orientation of a surgical robot based on an image including the robot marker mounted to a base of the surgical robot,
derive a third correlation between the position and the orientation of the robot marker and a position and an orientation of a work space, and
derive a fourth correlation between the position and the orientation of the surgical target and the position and the orientation of the work space based on tracking information about the positions and the orientations of the target marker and the robot marker, and the first, second and third correlations;
a graphic card configured to generate a graphic based on guide information about the fourth correlation; and
a display configured to display an image based on the guide information,
wherein the work space comprises a work orientation space and a work position space,
wherein the guide information comprises a first menu image showing whether the orientation of the surgical target is within the work orientation space, and a second menu image showing whether the position of the surgical target is within the work position space,
wherein the first menu image includes a first bar for indicating an X-angle, a second bar for indicating a Y-angle, and a third bar for indicating a Z-angle,
wherein the orientation of the surgical target is represented as points on corresponding angles on the first bar, the second bar, and the third bar, respectively, and
wherein the work orientation space is represented as a line in corresponding range on the first bar, the second bar, and the third bar.

2. The device of claim 1, wherein the guide information comprises information about a separation distance between the position of the surgical target and the work space.

3. The device of claim 2, wherein the position of the surgical target on the second menu image is represented with the surgical target comprising an area, which is within an operation path previously planned for the surgical target with respect to an origin of the operation path, based on the operation path.

4. The device of claim 3, wherein
the work space is calculated based on information about the position and the orientation of the surgical robot, and
the work position space is formed to have a volume with respect to an origin of the work space, and the work orientation space is based on the orientation of the surgical robot.

5. A system for guiding a position of a robot, comprising:
a tracker configured to track positions and orientations of a robot marker mounted to a base of a surgical robot and a target marker attached to a surgical target;
a memory configured to store a surgical target image of the surgical target, obtained before an operation;
at least one processor configured to
derive a first correlation between a position and an orientation of the surgical target and a position and an orientation of the target marker attached to the surgical target based on the surgical target image,
derive a second correlation between a position and an orientation of the robot marker and a position and an orientation of the surgical robot,
derive a third correlation between the position and the orientation of the robot marker and a position and an orientation of a work space, and
derive a fourth correlation between the position and the orientation of the work space and the position and the orientation of the surgical target based on tracking information about the positions and the orientations of the target marker and the robot marker obtained by the tracker, and the first, second, and third correlations;
a graphic card configured to generate a graphic based on guide information about the fourth correlation; and
a display configured to display an image based on the guide information,
wherein the work space comprises a work orientation space and a work position space,
wherein the guide information comprises a first menu image showing whether the orientation of the surgical target is within the work orientation space, and a second menu image showing whether the position of the surgical target is within the work position space,
wherein the first menu image includes a first bar for indicating an X-angle, a second bar for indicating a Y-angle, and a third bar for indicating a Z-angle,
wherein the orientation of the surgical target is represented as points on corresponding angles on the first bar, the second bar, and the third bar, respectively, and
wherein the work orientation space is represented as a line in corresponding range on the first bar, the second bar, and the third bar.

6. A method of guiding a position of a robot, comprising:
deriving a first correlation between a position and an orientation of a surgical target and a position and an orientation of a target marker attached to the surgical target by matching an image comprising the target marker attached to the surgical target with a surgical target image of the surgical target of before an operation;

deriving a second correlation between a position and an orientation of a robot marker and a position and an orientation of a surgical robot based on an image including the robot marker mounted to a base of the surgical robot;

deriving a third correlation between the position and the orientation of the robot marker and a position and an orientation of a work space; and deriving a fourth correlation between the position and the orientation of the surgical target and the position and the orientation of the work space based on tracking information about the positions and the orientations of the target marker and the robot marker, and the first, second, and third correlations; and displaying an image by generating a graphic based on guide information about the fourth correlation, wherein the work space comprises a work orientation space and a work position space, wherein the guide information comprises a first menu image showing whether the orientation of the surgical target is within the work orientation space, and a second menu image showing whether the position of the surgical target is within the work position space, wherein the first menu image includes a first bar for indicating an X-angle, a second bar for indicating a Y-angle, and a third bar for indicating a Z-angle, wherein the orientation of the surgical target is represented as points on corresponding angles on the first bar, the second bar, and the third bar, respectively, and wherein the work orientation space is represented as a line in corresponding range on the first bar, the second bar, and the third bar.

7. The method of claim 6, wherein the position of the surgical target on the second menu image is represented with the surgical target comprising an area, which is within an operation path previously planned for the surgical target with respect to an origin of the operation path, based on the operation path.

8. The method of claim 6, wherein the work space is calculated based on information about the position and the orientation of the surgical robot, and the work position space is formed to have a volume with respect to an origin of the work space, and the work orientation space is based on the orientation of the surgical robot.

9. A method of guiding a position of a robot, comprising:

deriving a first correlation between a position and an orientation of a robot marker and a position and an orientation of a surgical robot based on an image including the robot marker mounted to the surgical robot;

deriving a second correlation between the position and the orientation of the robot marker and a position and an orientation of a work space; and deriving a third correlation between a position and an orientation of a surgical target and a position and an orientation of a target marker attached to the surgical target by matching an image comprising the target marker attached to a base of the surgical target with a surgical target image of the surgical target of before an operation;

deriving a fourth correlation between the position and the orientation of the surgical target and the position and the orientation of the work space based on tracking information about the positions and the orientations of the target marker and the robot marker, and the first, second, and third correlations; and displaying an image by generating a graphic based on guide information about the fourth correlation, wherein the work space comprises a work orientation space and a work position space, wherein the guide information comprises a first menu image showing whether the orientation of the surgical target is within the work orientation space, and a second menu image showing whether the position of the surgical target is within the work position space, wherein the first menu image includes a first bar for indicating an X-angle, a second bar for indicating a Y-angle, and a third bar for indicating a Z-angle, wherein the orientation of the surgical target is represented as points on corresponding angles on the first bar, the second bar, and the third bar, respectively, and wherein the work orientation space is represented as a line in corresponding range on the first bar, the second bar, and the third bar.

10. The method of claim 9, wherein the position of the surgical target on the second menu image is represented with the surgical target comprising an area, which is within an operation path previously planned for the surgical target with respect to an origin of the operation path, based on the operation path.

11. The method of claim 9, wherein the work space is calculated based on information about the position and the orientation of the surgical robot, and the work position space is formed to have a volume with respect to an origin of the work space, and the work orientation space is based on the orientation of the surgical robot.

* * * * *